(12) United States Patent
Haney et al.

(10) Patent No.: US 8,480,389 B2
(45) Date of Patent: Jul. 9, 2013

(54) SPACER MOLD AND METHODS THEREFOR

(75) Inventors: Sean Haney, North Canton, OH (US);
Scott M. Sporer, Wheaton, IL (US);
Michael E. Hawkins, Columbia City, IN (US)

(73) Assignee: Zimmer Orthopedic Surgical Products, Inc., Dover, OH (US)

( * ) Notice: Subject to any disclaimer, the term of this patent is extended or adjusted under 35 U.S.C. 154(b) by 0 days.

(21) Appl. No.: 12/833,346

(22) Filed: Jul. 9, 2010

(65) Prior Publication Data
US 2010/0297276 A1    Nov. 25, 2010

Related U.S. Application Data

(63) Continuation of application No. 12/328,062, filed on Dec. 4, 2008, now Pat. No. 7,789,646.

(60) Provisional application No. 61/012,082, filed on Dec. 7, 2007.

(51) Int. Cl.
*B29C 33/12* (2006.01)
*B29C 33/44* (2006.01)

(52) U.S. Cl.
USPC ............... 425/117; 249/55; 249/61; 249/91; 249/158

(58) Field of Classification Search
USPC ................ 249/55, 61, 83, 91, 158; 425/117, 425/567
See application file for complete search history.

(56) References Cited

U.S. PATENT DOCUMENTS

| 529,309 | A | * | 11/1894 | Ramming ............... 249/158 |
|---|---|---|---|---|
| 1,520,849 | A | | 12/1924 | Birnbach |
| 1,612,133 | A | | 12/1926 | Lee |
| 3,774,244 | A | | 11/1973 | Walker |
| 3,816,855 | A | | 6/1974 | Saleh |
| 3,964,106 | A | | 6/1976 | Hutter, Jr. et al. |
| 4,016,606 | A | | 4/1977 | Murray et al. |
| 4,059,684 | A | | 11/1977 | Gross et al. |
| 4,191,740 | A | | 3/1980 | Heusser et al. |
| 4,297,993 | A | | 11/1981 | Harle |
| 4,373,217 | A | | 2/1983 | Draenert |
| 4,610,692 | A | | 9/1986 | Eitenmuller et al. |
| 4,615,705 | A | | 10/1986 | Scales et al. |

(Continued)

FOREIGN PATENT DOCUMENTS

| DE | 29703971 U1 | 7/1998 |
|---|---|---|
| EP | 0378928 A1 | 7/1990 |

(Continued)

OTHER PUBLICATIONS

PCT Search Report from related PCT/US2008/085527; Jul. 13, 2009; 17 pages.

(Continued)

*Primary Examiner* — Robert B Davis
(74) *Attorney, Agent, or Firm* — Schwegman, Lundberg & Woessner P.A.

(57) ABSTRACT

A hip spacer mold forming a spacer with a spacer stem connected to a spacer head has a stem portion for forming a spacer stem. The hip spacer mold also has a plurality of interchangeable head modules configured for alternatively forming spacer heads of a plurality of different predetermined sizes. The head modules are configured to be disposed adjacent the stem portion.

25 Claims, 11 Drawing Sheets

U.S. PATENT DOCUMENTS

| | | |
|---|---|---|
| 4,717,115 A | 1/1988 | Schmitz |
| 4,749,585 A | 6/1988 | Greco et al. |
| 4,815,960 A | 3/1989 | Rudolph |
| 4,822,365 A | 4/1989 | Walker et al. |
| 4,843,112 A | 6/1989 | Gerhart et al. |
| 4,853,225 A | 8/1989 | Wahlig et al. |
| 4,882,149 A | 11/1989 | Spector |
| 4,900,546 A | 2/1990 | Posey-Dowty et al. |
| 4,919,666 A | 4/1990 | Buchhorn et al. |
| 4,919,679 A | 4/1990 | Averill et al. |
| 4,959,071 A | 9/1990 | Brown et al. |
| 5,030,237 A | 7/1991 | Sorbie et al. |
| 5,033,712 A | 7/1991 | Ravet |
| 5,059,209 A | 10/1991 | Jones |
| 5,061,286 A | 10/1991 | Lyle |
| 5,098,620 A | 3/1992 | Bradley et al. |
| 5,106,614 A | 4/1992 | Posey-Dowty et al. |
| 5,123,927 A | 6/1992 | Duncan et al. |
| 5,133,771 A | 7/1992 | Duncan et al. |
| 5,151,279 A | 9/1992 | Kimura |
| 5,171,282 A | 12/1992 | Pequignot |
| 5,197,986 A | 3/1993 | Mikhail |
| 5,226,915 A | 7/1993 | Bertin |
| 5,236,457 A | 8/1993 | Devanathan |
| 5,286,763 A | 2/1994 | Gerhart et al. |
| 5,501,687 A | 3/1996 | Willert et al. |
| 5,549,684 A | 8/1996 | Amino et al. |
| 5,681,289 A | 10/1997 | Wilcox et al. |
| 5,693,099 A | 12/1997 | Härle |
| 5,980,573 A | 11/1999 | Shaffner |
| 6,155,812 A | 12/2000 | Smith et al. |
| 6,193,493 B1 | 2/2001 | Steijer et al. |
| 6,245,111 B1 | 6/2001 | Shaffner |
| 6,361,731 B1 | 3/2002 | Smith et al. |
| 6,506,217 B1 | 1/2003 | Arnett |
| 6,540,786 B2 | 4/2003 | Chibrac et al. |
| 6,755,563 B2 | 6/2004 | Wahlig et al. |
| 6,787,097 B1 | 9/2004 | Homann et al. |
| 6,821,470 B2 | 11/2004 | Gundlapalli et al. |
| 6,887,276 B2 | 5/2005 | Gerbec et al. |
| 6,905,582 B2 | 6/2005 | Kidd et al. |
| 6,916,308 B2 | 7/2005 | Dixon et al. |
| 6,942,475 B2 | 9/2005 | Ensign et al. |
| 7,070,622 B1 | 7/2006 | Brown et al. |
| 7,077,867 B1 | 7/2006 | Pope et al. |
| 7,109,254 B2 | 9/2006 | Muller et al. |
| 7,153,327 B1 | 12/2006 | Metzger |
| 7,255,715 B2 | 8/2007 | Metzger |
| 7,320,709 B2 | 1/2008 | Felt et al. |
| 7,326,252 B2 | 2/2008 | Otto et al. |
| 7,338,529 B1 | 3/2008 | Higgins |
| 7,427,296 B2 | 9/2008 | Evans |
| 7,429,346 B2 | 9/2008 | Ensign et al. |
| 7,575,602 B2 | 8/2009 | Amirouche et al. |
| 7,601,176 B2 | 10/2009 | Soffiati et al. |
| 7,789,646 B2 | 9/2010 | Haney et al. |
| 2002/0010431 A1 | 1/2002 | Dixon et al. |
| 2003/0009230 A1 | 1/2003 | Gundlapalli et al. |
| 2003/0009231 A1 | 1/2003 | Gundlapalli et al. |
| 2003/0021180 A1 | 1/2003 | Wahlig et al. |
| 2003/0075564 A1 | 4/2003 | Wahlig et al. |
| 2003/0103408 A1 | 6/2003 | Foster |
| 2004/0036189 A1 | 2/2004 | Ensign et al. |
| 2004/0054417 A1 | 3/2004 | Soffiati et al. |
| 2004/0066706 A1 | 4/2004 | Barker et al. |
| 2004/0083003 A1 | 4/2004 | Wasielewski |
| 2004/0196735 A1 | 10/2004 | Barker et al. |
| 2004/0236424 A1 | 11/2004 | Berez et al. |
| 2004/0236429 A1 | 11/2004 | Ensign et al. |
| 2004/0249382 A1 | 12/2004 | Olson, Jr. et al. |
| 2005/0033424 A1 | 2/2005 | Fell |
| 2005/0085918 A1 | 4/2005 | Soffiati et al. |
| 2005/0096747 A1 | 5/2005 | Tuttle et al. |
| 2005/0107885 A1 | 5/2005 | Evans |
| 2005/0119756 A1 | 6/2005 | Soffiati et al. |
| 2005/0171604 A1 | 8/2005 | Michalow |
| 2006/0004431 A1 | 1/2006 | Fuller et al. |
| 2006/0093646 A1 | 5/2006 | Cima et al. |
| 2007/0100450 A1 | 5/2007 | Hodorek |
| 2007/0100462 A1 | 5/2007 | Lang et al. |
| 2007/0104819 A1 | 5/2007 | Ness et al. |
| 2007/0141106 A1 | 6/2007 | Bonutti et al. |
| 2007/0142392 A1 | 6/2007 | Murphy et al. |
| 2007/0162144 A1 | 7/2007 | Wasielewski |
| 2007/0213835 A1 | 9/2007 | Wimmer et al. |
| 2007/0213853 A1 | 9/2007 | Glanzer |
| 2007/0222114 A1 | 9/2007 | Ziran et al. |
| 2007/0233266 A1 | 10/2007 | Williams, III et al. |
| 2007/0270447 A1 | 11/2007 | Hunter et al. |
| 2007/0282451 A1 | 12/2007 | Metzger et al. |
| 2008/0027431 A1 | 1/2008 | Williams et al. |
| 2008/0058950 A1 | 3/2008 | Leonard et al. |
| 2008/0086210 A1 | 4/2008 | Fox |
| 2008/0097605 A1 | 4/2008 | Pastorello et al. |
| 2008/0097606 A1 | 4/2008 | Cragg et al. |
| 2008/0119931 A1 | 5/2008 | Fell et al. |
| 2008/0133020 A1 | 6/2008 | Blackwell et al. |
| 2008/0269909 A1 | 10/2008 | Vogt et al. |
| 2009/0234459 A1 | 9/2009 | Sporring et al. |
| 2009/0295035 A1 | 12/2009 | Evans |
| 2010/0102484 A1 | 4/2010 | Haney et al. |
| 2010/0185298 A1 | 7/2010 | Stone |
| 2010/0292803 A1 | 11/2010 | Giori |
| 2010/0297276 A1 | 11/2010 | Haney et al. |
| 2011/0054481 A1 | 3/2011 | Sproul |
| 2011/0071072 A1 | 3/2011 | Calderone et al. |

FOREIGN PATENT DOCUMENTS

| | | |
|---|---|---|
| EP | 0602274 A1 | 6/1994 |
| EP | 0811359 A2 | 12/1997 |
| EP | 1952787 A1 | 8/2008 |
| EP | 1082199 B1 | 9/2008 |
| EP | 1274374 B1 | 12/2008 |
| EP | 2298696 A1 | 3/2011 |
| EP | 1919401 B1 | 4/2011 |
| JP | 02065858 A2 | 3/1990 |
| JP | 2001017454 | 1/2001 |
| JP | 2006015042 A1 | 1/2006 |
| WO | 98/51240 A1 | 11/1998 |
| WO | WO-9851240 A1 | 11/1998 |
| WO | 00/03855 A1 | 1/2000 |
| WO | 01/54561 A1 | 8/2001 |
| WO | WO01/76512 A1 | 10/2001 |
| WO | WO03/086241 A1 | 10/2003 |
| WO | 2005025451 A2 | 3/2005 |
| WO | WO2006/090226 A1 | 8/2006 |
| WO | 2007005667 A2 | 1/2007 |
| WO | 2007056667 A2 | 5/2007 |
| WO | WO-2007056667 A2 | 5/2007 |
| WO | 2007084878 A1 | 7/2007 |
| WO | WO-2007084878 A1 | 7/2007 |
| WO | 2007136417 A2 | 11/2007 |
| WO | 2007144667 A2 | 12/2007 |
| WO | 2008020904 A2 | 2/2008 |
| WO | 2009073781 A2 | 6/2009 |
| WO | WO2009/076168 A1 | 6/2009 |
| WO | WO2010015877 A1 | 2/2010 |

OTHER PUBLICATIONS

PCT Search Report from related PCT/US2008/085538; Jun. 18, 2009; 11 pages.

Goodell et al., "Preparation and Release Characteristics of Tobramycin-impregnated Polymethylmethacrylate Beads," American Journal of Hospital Pharmacy; vol. 43, Jun. 1986, p. 1454-1461.

Cohen et al., "Two-Stage Reimplantation of Septic Total Knee Arthroplasty," The Journal of Arthroplasty; vol. 3, No. 4, 1988, p. 369-377.

Booth et al., "The Results of Spacer Block Technique in Revision of Infected Total Knee Arthroplasty," Clinical Orthopaedics and Related Research; 1989, p. 57-60.

Henderson et al., "The Use of an Antibiotic-Impregnated Spacer Block for Revision of the Septic Total Knee Arthroplasty," Seminars in Arthroplasty, vol. 2, No. 1, Jan. 1991, p. 34-39.

Abstract of IT 1278853 B1 published Mar. 1997.

"U.S. Appl. No. 12/328,062, Non Final Office Action mailed Dec. 24, 2009", 9 pgs.

"U.S. Appl. No. 12/328,062, Notice of Allowance mailed Apr. 29, 2010", 4 pgs.

"U.S. Appl. No. 12/328,062, Response filed Apr. 8, 2010 to Non Final Office Action mailed Dec. 24, 2009", 5 pgs.

"U.S. Appl. No. 12/328,062, Response filed Dec. 3, 2009 to Restriction Requirement mailed Oct. 6, 2009", 2 pgs.

"U.S. Appl. No. 12/328,062, Restriction Requirement mailed Oct. 6, 2009", 6 pgs.

"Canadian Application Serial No. 2,719,033, Response filed Sep. 21, 2012 to Office Action mailed Mar. 22, 2012", 5 pgs.

* cited by examiner

SPACER MOLD AND METHODS THEREFOR

CROSS-REFERENCE TO RELATED APPLICATIONS

This Continuation application claims priority from U.S. non-provisional application Ser. No. 12/328,062, filed Dec. 4, 2008, which issued as U.S. Pat. No. 7,789,646 on Sep. 7, 2010 and which claims the benefit of U.S. Provisional Application Ser. No. 61/012,082, filed Dec. 7, 2007, the contents of which are incorporated herein by reference in their entirety for all purposes.

FIELD OF THE INVENTION

The present invention is directed to molds for forming orthopedic implants and, more particularly, to molds for forming temporary spacer orthopedic implants.

BACKGROUND OF THE INVENTION

From time to time, orthopedic implants such as knee or hip replacements and the tissue around the implant become infected. The infected implant is removed, and it conventionally takes 4 to 8 weeks or more to adequately treat the infection during which time the implant site is kept immobile. This may cause unused muscles to contract and shrink the space previously occupied by the joint implant that connected articulating bones such as the space between the shortened end of a femur and the acetabulum on the hip bone in the case of a hip replacement.

To prevent the shrinkage of the implant site, one treatment is to replace the infected permanent implant with a temporary implant or spacer made of an antibiotic-filled cement. The spacer preserves the distance between the adjoining bones so that muscle cannot overly contract while the infection is being cleared from the implant site. Additionally, once positioned within the body, the antibiotic leaches out of the spacer to treat tissue near the spacer and prevent further spreading of the infection. Once the infection is cleared, the spacer is replaced with a new permanent implant.

Some known spacers are pre-made and are provided to the physicians performing the surgery. This usually provides little or no opportunity for the physicians to significantly customize or modify the spacer to match the size of a patient's implant site during the surgical procedures for implanting the spacer.

Other spacers are molded by the physicians by filling molds with curable cement during the surgical procedure. In these cases, when hard molds are used, substantial customization is not possible when the wrong size mold is provided. Also, relatively cumbersome, time consuming, and messy procedures are used to fill the molds. For instance, such hard molds are usually filled by pouring the antibiotic filled cement into mold pieces and then placing the cement into all spaces in the mold by using a spoon or spatula.

Other known relatively soft silicone spacer molds are enclosed for injecting cement into the mold from a cement gun with a nozzle. To fill all of the spaces in the enclosed mold, extra time and effort by the physician is required to shift the nozzle of the cement gun in different directions within the mold. Thus, a spacer mold is desired that permits physicians to easily select and adjust the size of the spacer mold even during surgical procedures, and efficiently and cleanly fill the spacer mold.

DETAILED DESCRIPTION OF THE PREFERRED EMBODIMENTS

Figure 1:
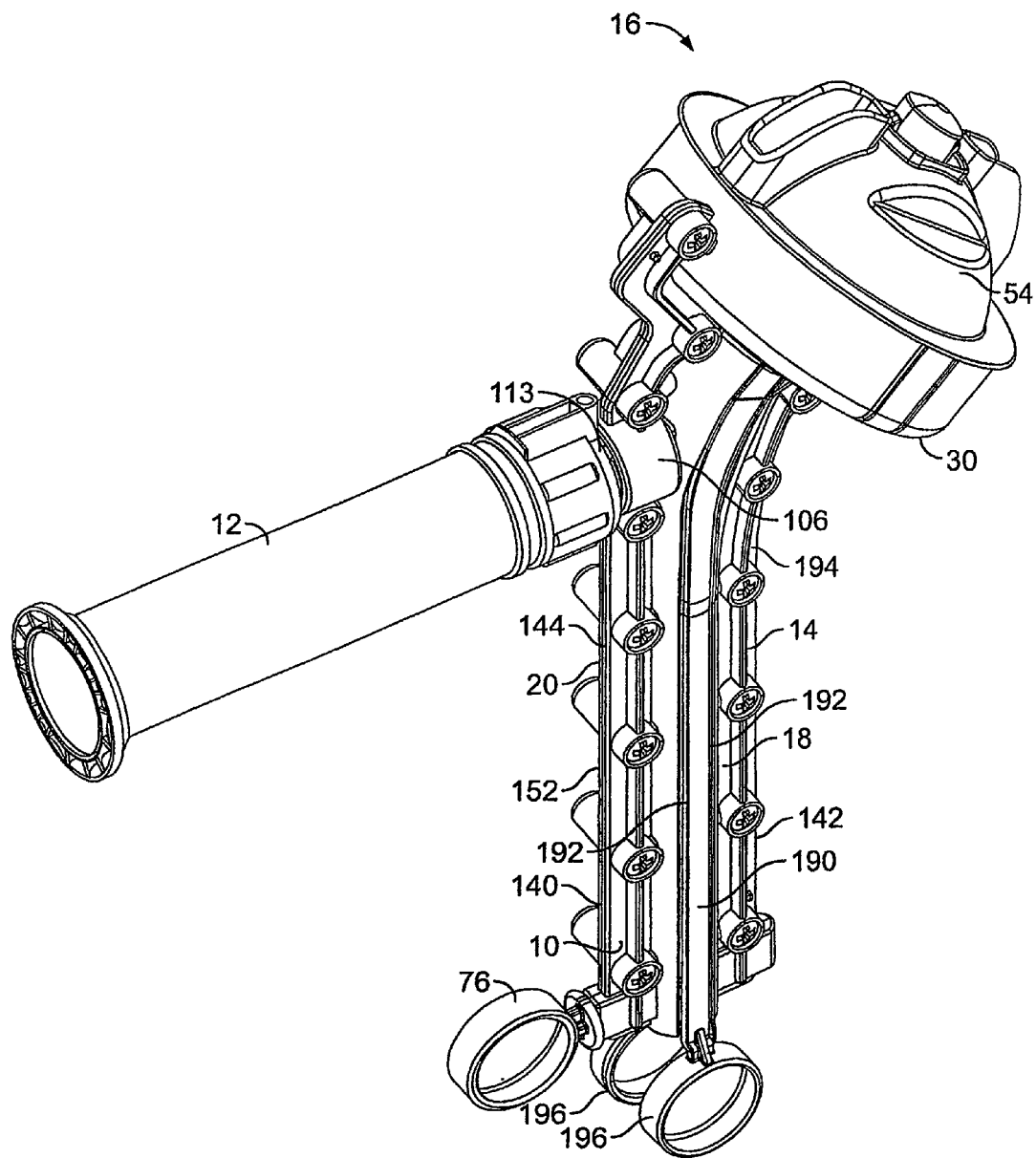
FIG. 1 is a left side perspective view of a spacer mold connected to a cement gun in accordance with the present invention.
Figure 2:
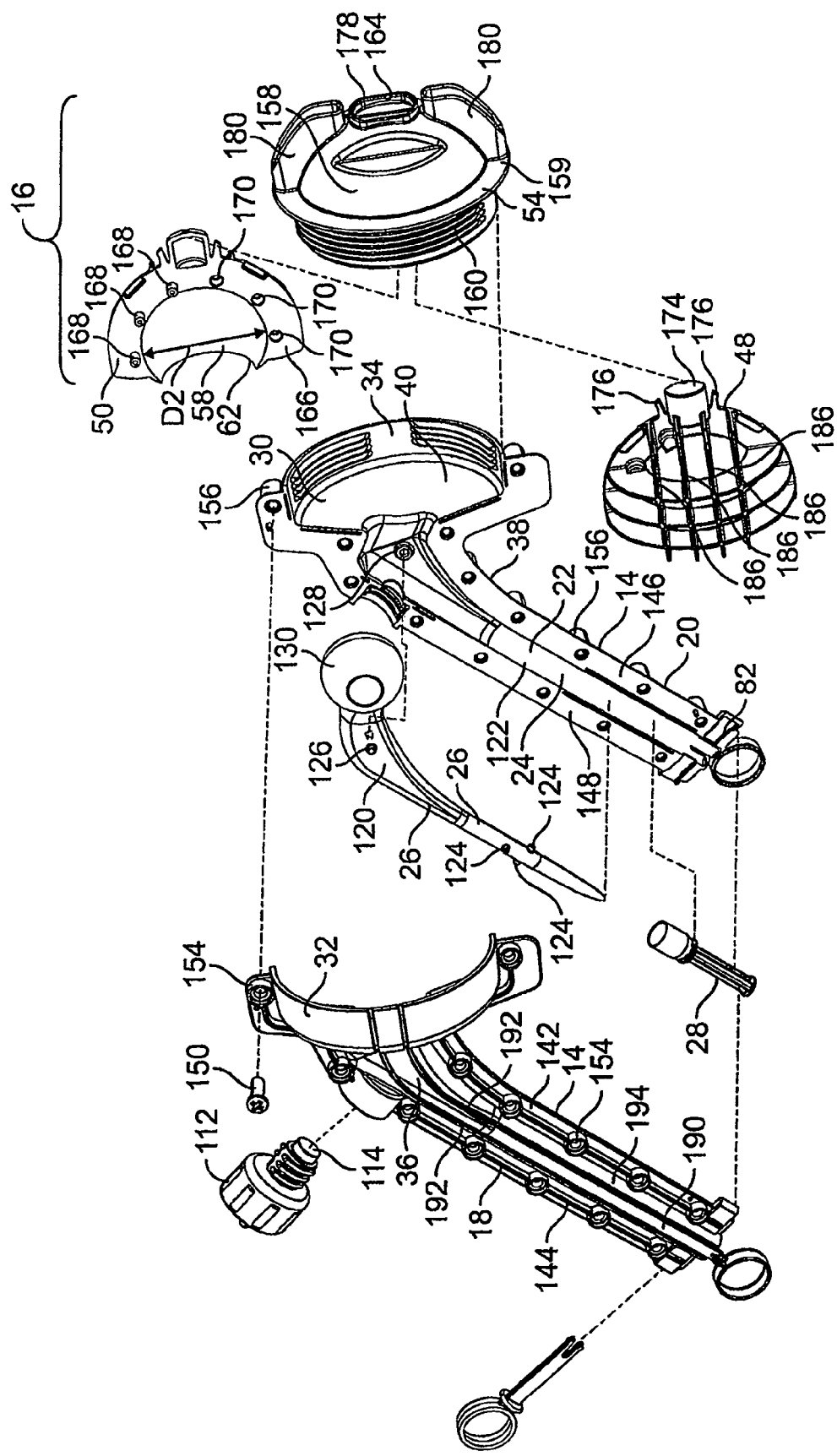
FIG. 2 is an exploded perspective view of the spacer mold of FIG. 1.
Figure 3:
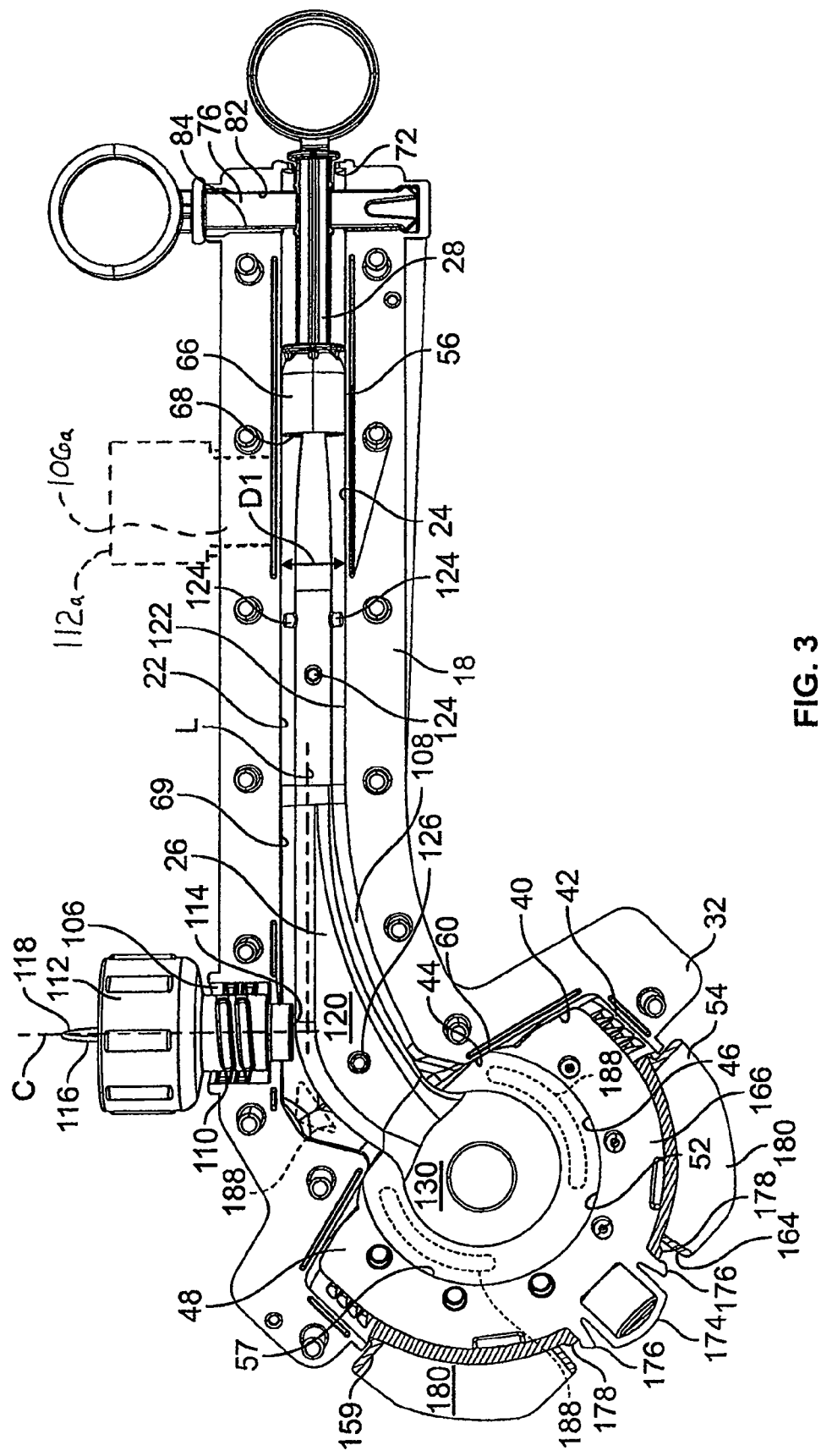
FIG. 3 is a right side elevational view of the spacer mold of FIG. 1 with a right part removed and an upper cover shown in cross-sectional view.
Figure 12:
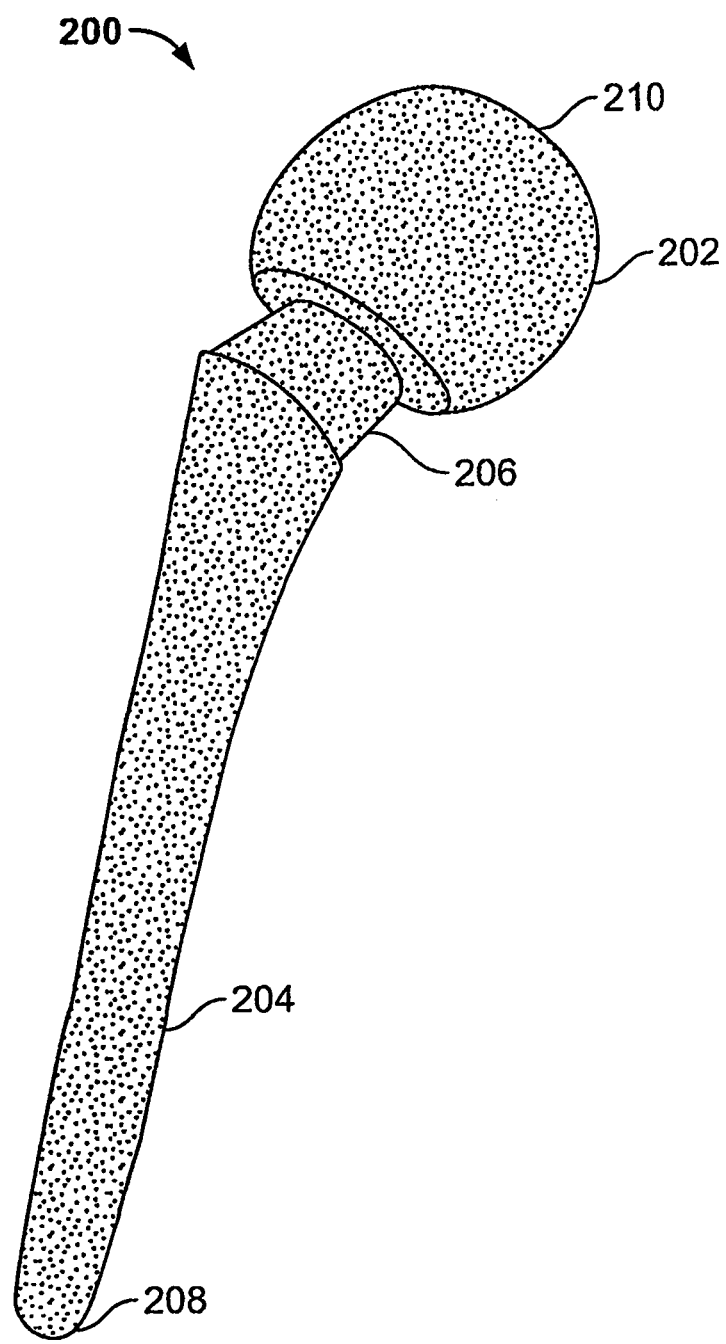
FIG. 12 is a left side perspective view of a spacer formed by the spacer mold of FIG. 1 in accordance with the present invention.

Referring to FIGS. 1-3, a spacer mold 10 is releasably connected to a pressurized cement cartridge 12 that fits on a cement gun such as a Zimmer's PowerFlo® Bone Cement Injector that uses pressurized cartridges of cement connected to a nozzle, for example. The cement gun can eject cement from cartridge 12 such as high-strength, high-viscosity PMMA. This includes materials such as Palacos® R+G High Viscosity Bone Cement and any other similar material (as used herein, the term 'cement' generally refers to any curing and hardening material suitable for implanted spacers unless noted otherwise). The cement may be loaded with an antibiotic such as Gentamicin and/or clindamycin in order to clear infection from tissue surrounding an implanted spacer formed by spacer mold 10. As shown in FIG. 12, for one embodiment, a hip spacer 200 formed by spacer mold 10 has a spacer head 202 connected to, or integrally formed with, a spacer stem 204. A bent neck 206 connects the spacer head 202 to the spacer stem 204 to match the shape of the superior portion of a femur. The spacer mold 10 has a stem portion 14 used to form the spacer stem 204, and a head portion 16 used to form the spacer head 202.

In one form, the stem portion 14 includes corresponding left and right stem members 18 and 20 that may be mirror images of each other or may have different shapes. The left and right stem members 18 and 20 are configured to mate and cooperatively define a main, longitudinally extending cavity or space 22 between them to form the spacer stem 204 in the cavity 22. The stem members 18 and 20 each have an aligning symmetrical groove 24 (only the groove 24 on the right stem member 20 is shown in FIG. 2) to form the cavity 22. The cavity 22 also may receive a reinforcing bar 26 to be embedded within the spacer 200 when it is formed, and a stem-end mold piece 28 (also referred to as a stem plug) for forming the inferior end 208 of the spacer stem 204 that is to be implanted on a femur.

Figure 4:
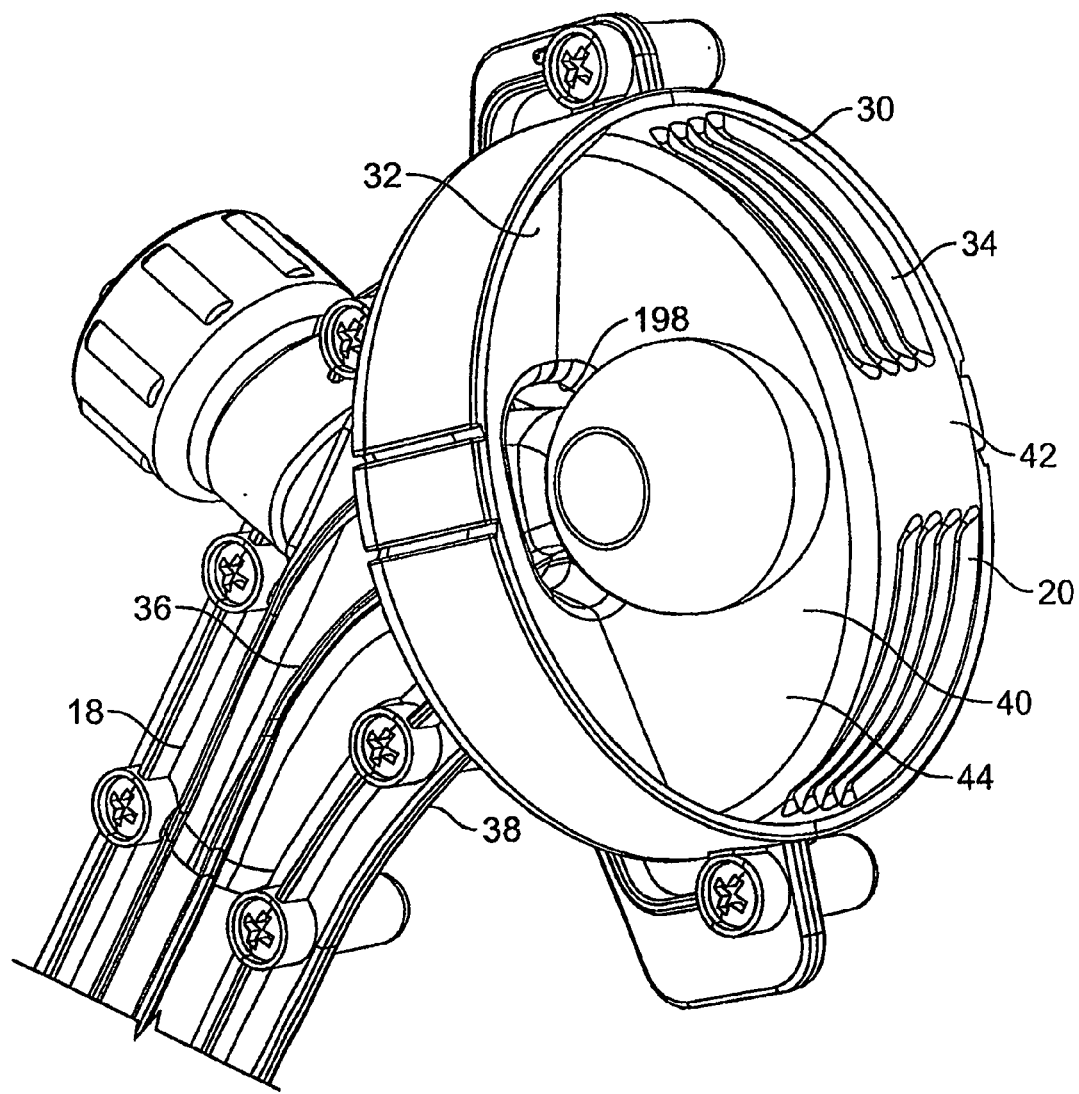
FIG. 4 is fragmentary perspective view of an end of a stem portion of the spacer mold of FIG. 1 with a head portion removed.

Referring to FIG. 4, a superior end portion 30 of the stem portion 14 includes two corresponding, widened sections 32 and 34 of the stem members 18 and 20, respectively. In the illustrated form, the widened sections 32 and 34 respectively extend radially outward from generally longitudinally extending outer surfaces 36 and 38 of the stem members 18 and 20. The superior end portion 30 generally forms a bowl shape with a generally circular, surface or bottom 40 and a cylindrical wall 42 extending longitudinally or outwardly from the bottom 40. The bowl-shaped superior end portion 30 defines a bottom or lower portion 44 of a head molding chamber 46 (shown in FIG. 3) used to mold the spacer head 202 therein. The bottom 40 provides the bottom of the head molding chamber 46.

Referring to FIGS. 2-3, one or more head modules are provided, but in this example two head modules 48 and 50 are received within the superior end portion 30 and cooperatively define an upper portion 52 of the head molding chamber 46. A securing member 54 releasably holds the head modules 48 and 50 adjacent the stem portion 14, and more specifically, against the bottom 44 of the head molding chamber 46. While the securing member 54 also covers the head modules 48 and 50, it will be understood that this is not necessary in all cases as long as the securing member 54 keeps the head modules 48 and 50 adjacent to the stem portion 14 or in generally fixed relation to the stem portion 14 while receiving pressurized cement during filling of the spacer mold 10 and setting of the cement within the head molding chamber 46.

To properly match the actual size of a hip joint implant site, the stem portion 14 may be provided in different sizes. In one form, a plurality of stem portions 14 are available where each stem portion has a different predetermined inner diameter for the cavity 22, such as 12 mm, 14 mm, 16 mm, or 18 mm to name just a few examples, to mold spacers with those dimensions. In this case, the inner diameter may be a generally uniform diameter D1 (shown on FIG. 3) of a lower or inferior section 56 of the stem portion 14. Alternatively, a diameter may be measured at a maximum or minimum location on the stem portion 14 especially when the cavity 22 generally tapers inward or outward.

It will be understood that other dimensions may be varied on the stem portion 14 such as additionally or alternatively providing different axial lengths or a variation in any other dimension for the internal cavity 22 that would be convenient to have available in different sizes. A stem portion 14 with a desired size may be ordered from the manufacturer after the implant site is conveniently measured with X-rays, imaging, or other non-evasive scanning technology. Otherwise, in one example, a plurality of the stem portions 14 may be provided in a kit so that the surgeon can use the closest fitting stem portion during a surgical procedure when the implant site is open and accessible for measurement.

To add even further adaptability, the head modules 48 and 50 also are provided in different predetermined sizes and are interchangeable on the stem portion 14. In the illustrated form, head modules 48 and 50 each have a concave, arcuate, internal surface 57 (shown in FIGS. 3) and 58 (shown in FIG. 2), respectively, that are contiguous with each other to cooperatively form a generally continuous molding surface to form the upper portion 52 of the head molding chamber 46. The surfaces 57 and 58 mold at least a portion of a rounded or spherical outer surface 210 of the spacer head 202. In one form, the surfaces 57 and 58 extend on the head modules 48 and 50 to provide the outer surface 210 of the spacer head with a shape that is generally about ¾ of a sphere or otherwise matches an articular surface of a femur head. The surfaces 57 and 58 respectively terminate at lower, arcuate surfaces, or ends 60 and 62 (also shown in FIG. 11) of the head modules 48 and 50 and are configured to seat on the bottom 44 of the head molding chamber 46.

The internal surfaces 57 and 58 have a matching internal diameter D2 (shown on FIG. 2). Thus, it will be understood that only one head module may be needed for a spacer mold 10 instead of two matching head modules, or more than two head modules may be used on a single spacer mold. No matter the number of head modules, a set of head modules may be provided where each head module (or each pair (or other number) of matching head modules) alternatively provide a different inner diameter D2. In one example form, a set of pairs of head modules may provide inner diameters D2 of approximately 50 mm, 53 mm, 56 mm, 59 mm, 62 mm, or 65 mm. When such a set is provided during a surgical procedure, the surgeon may measure the diameter of the acetabulum, or the remaining void on the hip when an implanted acetabular cup is removed from the hip to clear the infection, and then find the head module or modules with the closest matching inner diameter D2.

In one embodiment, while the inner diameter D2 may vary from head module to head module (or from pair to pair of head modules), the head modules will all have the same or similar exterior dimensions so that they all fit on any size stem portion 14 to provide maximum adaptability. Of course, other configurations are contemplated where only certain head module sizes can be used with stem portions of a certain size.

Figure 6:
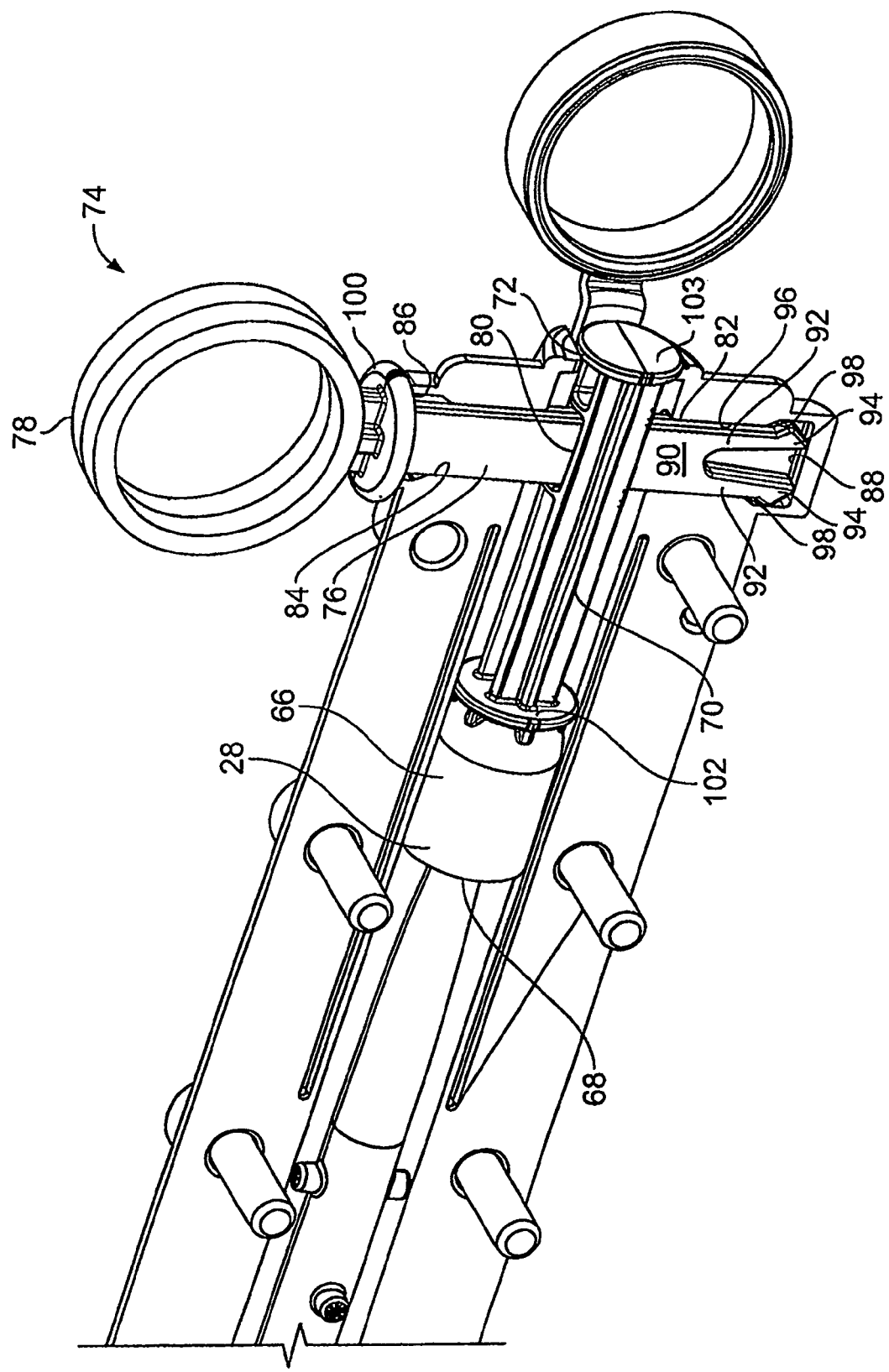
FIG. 6 is a fragmentary, close-up, right side perspective view of an end of the spacer mold of FIG. 1 with a right part and a screw removed.
Figure 7:
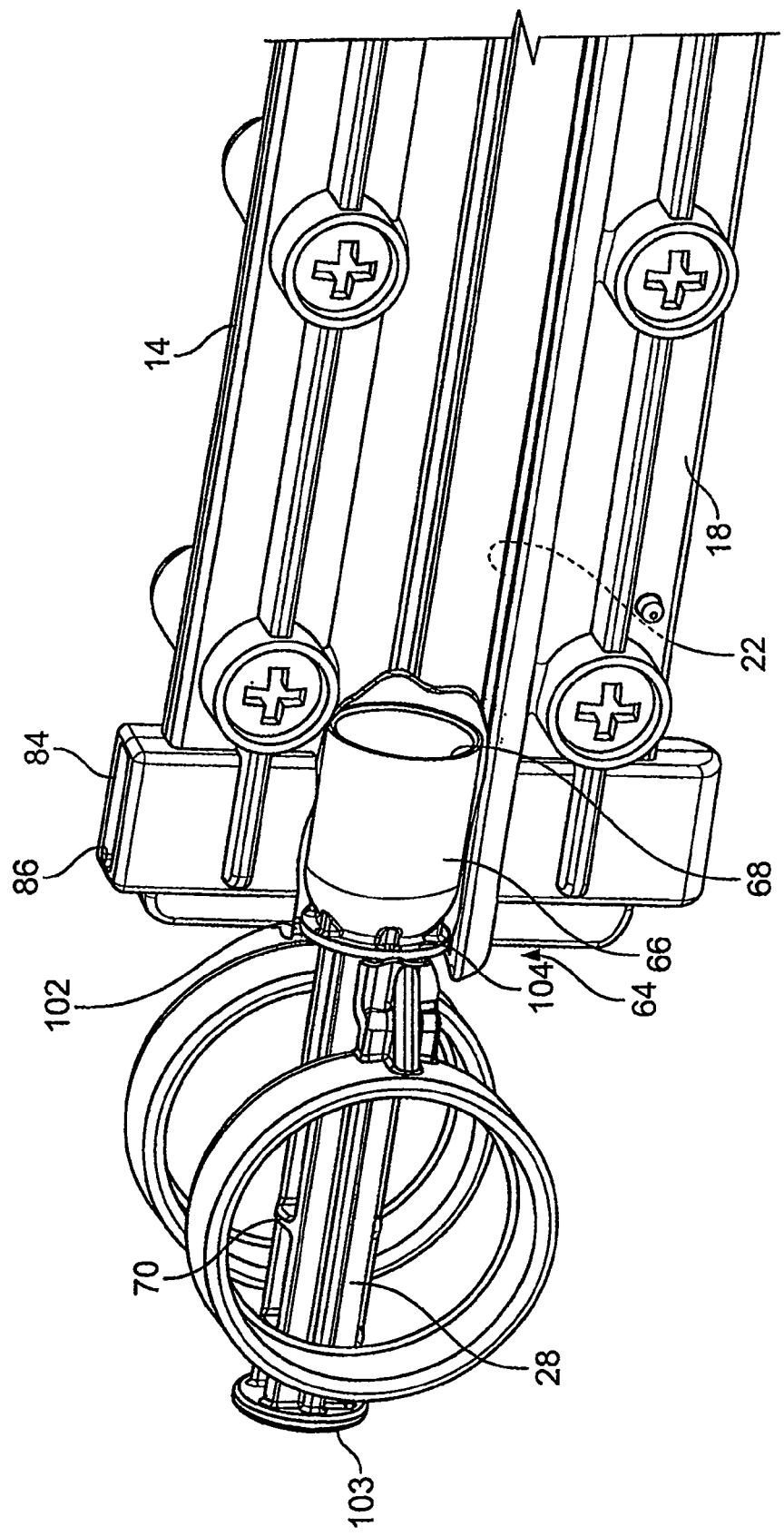
FIG. 7 is a fragmentary, cut-away left side view of an end of the spacer mold of FIG. 1 showing the retention of an adjustable part in accordance with the present invention.

Referring to FIGS. 3 and 6-7, the stem portion 14 also provides the cavity 22 with an adjustable length. Generally, the stem portion 14 has a first member, such as the stem-end mold piece 28, and a second member, such as the stem portion 14, where the first and second members are movable relative to each other to adjust the length of the stem mold cavity. To this end, the stem-end mold piece 28 is received, at least in part, into the stem member or members 18 and 20 and is adjustable to a plurality of positions. Each position forms a different length for the stem mold cavity 22 to mold a spacer stem 204 of a different length.

More specifically, the stem-end mold piece 28 has a cup-shaped portion 66 with an opening 68 that faces toward a section of the cavity 22 from which cement will be flowing to the stem-end mold piece. In this case, the opening 68 faces an intermediate section 69 (shown in FIG. 3) of the cavity 22. The cup-shaped portion 66 is used to form the inferior end 208 of the spacer stem 204. An elongated handle portion 70 on the stem-end mold piece 28 extends from the cup portion 66 and longitudinally out of the stem portion 14 through a distal opening 72 cooperatively formed by the aligned stem members 18 and 20. With the handle portion 70 accessible, the stem portion 14 can be preassembled with the stem-end mold piece 78 already disposed with the stem portion 14 and a user can still manipulate the handle portion 70 to translate the stem-end mold piece 28 to a desired predetermined position within the cavity 22.

Referring to FIG. 6, the stem-end mold piece 28 is secured in one of the predetermined positions by a retaining mechanism 74, such as a pin 76 with a grasping ring 78 at one end. The handle portion 70 of the stem-end mold piece 28 has a hole or retaining surface 80 for releasably receiving the pin 76. To receive and hold the pin 76 on the stem portion 14, the stem members 18 and 20 each have a transversely extending, symmetrical groove 82 that align with each other to form a transverse passage or slot 84 with an opening 86 (shown best in FIG. 7) to receive the pin 76 and an enclosed bottom 88 opposite the opening 86. While the slot 84 is generally rectangular in cross-section, it may alternatively be a circular bore, or any other shape as long as the pin 76 is able to translate within and be secured within the slot.

The pin 76 has a connection portion 90 for releasably connecting the pin 76 to the stem portion 14. In one form, the connection portion 90 has two or more flexible fingers 92 with barbed ends 94. The fingers 92 are biased outward so that they can be flexed inward to move the pin 76 through the slot 84 and opening 80 on the handle portion 70. The slot 84 has a widened section 96 to provide clearance for the fingers 92 to shift back outward to their natural position once the pin 76 extends through the handle portion 70. In this position, the barbed ends 94 oppose tapered retaining surfaces 98 at the widened section 96 that retain the barbed ends 94 and in turn the pin 76 in the slot 84. This structure limits unintentional pull-out of the pin 76 from the slot 84 unless a user pulls on the grasping ring 78 with sufficient force. This cams the barbed ends 94 on the retaining surfaces 98 thereby transversely pressing the fingers 92 together to clear the retaining surfaces 98 and squeeze the pin 76 so that the pin 76 can be translated within the slot. The bottom 88 of the slot 84 limits further insertion of the pin 76 into the slot 84 as does a flange 100 on the pin 76 that has a width greater than the inner width of the slot 84.

As shown in FIG. 7, for another predetermined position for the stem-end mold piece 28 relative to the stem portion 14, the pin 76 is removed from slot 84 and the handle portion 70. In this case, a retaining mechanism 64 includes an outwardly, radially extending flange 102 of the handle portion 70 that engages an inner wall 104 integrally formed on the stem portion 14 that defines opening 72. The inner wall 104 secures the stem-end mold piece 28 on the stem portion 14. To retain the stem-end mold piece 28, the flange 102 has an outer dimension or width greater than an inner dimension or width of the opening 72. With the pin 76 removed, either a user can pull the stem-end mold piece 28 by the handle portion 70 and until the flange 102 engages the inner wall 104, or the pressure from cement filling the cavity 22 will push the stem-end piece 28 outward to engage the flange 102 to the inner wall 104. The handle portion 70 also has a distal flange 103 with an outer dimension greater than the inner dimension of the opening 72 on the inner wall 104 so that the distal flange 104 engages the inner wall 104 to restrict further translation of the stem-end mold piece 28 into the stem portion 14.

With the illustrated embodiment, the stem-end mold piece 28 is provided with at least two predetermined positions, one with the pin 76 engaged to the stem-end mold piece 28 (FIG. 6) and one without the pin 76 (FIG. 7). These two positions, in one form, provide for a change in the length of the cavity 22 and, in turn a resulting spacer stem length, of approximately 40 mm from a length of approximately 160 mm to about 200 mm. It will be appreciated as mentioned above, however, that the handle portion 70 may have multiple holes for receiving the pin 76 where each hole defines a different longitudinal position for the stem-end mold piece 28 to provide for more than two different spacer stem lengths. It will also be appreciated that other similar securing devices could be used instead of a pin such as, for example, locking tab and groove connections between stem-end mold piece 28 and stem members 18 and 20, an interference fit between the two, or even threaded connections between stem-end mold piece 28 and stem members 18 and 20 and/or between stem-end mold piece 28 and pin 76.

With four different stem portion sizes, six different head module sizes, and two different stem length sizes, at least 48 different spacer mold sizes are provided. It will be understood that depending on the sizes offered and modifications of the structure as mentioned above, more or less spacer mold sizes may be provided. Thus, while in one embodiment all three of (1) the modularity of the head modules, (2) the modularity of the stem portion, and (3) the adjustability of the stem length are provided, it will be understood that only one or two of any of these features may be provided instead.

Referring to FIGS. 1-4, the intermediate section 69 of the stem portion 14 also has a port 106 that provides access to the interior or cavity 22 of the stem portion 14 to receive cement injected from the cement gun and cartridge 12 or other injector of pressurized, curable material. The cement is provided from the cartridge 12 at a pressure sufficient to spread the cement to substantially fill the spacer mold 10. Specifically, the cement fills the lower end portion 56 of the stem portion 14, filling the cup-shaped portion 66 of the stem-end mold piece 28 and shifting the mold piece 28 outward if the pin 76 is not present. The cement also fills an upper portion 108 of the stem portion 14 forming the neck 206 of the spacer 200, and then fills the head molding chamber 46 within the head modules 48 and 50.

The port 106 is sufficiently rigid to remain connected to the cement gun while the cement is injected under relatively high pressure, such as, in one form, at approximately 300 psi to 350 psi. The remainder of the spacer mold 10 including the port 106 also has a sufficient rigidity to receive the cement under high pressure without compromising an effectiveness of the spacer mold and unintentional disconnect of an injector from the port 106. In other words, the port 106 and the rest of the spacer mold 10 will not break, split, or crack when the pressurized cement impacts the spacer mold 10. For these purposes, in one form, high density polyethylene is used to make the spacer mold 10.

The port 106 is also configured to permit the cement gun 12 to be detached from the port 106 after filling is complete. Thus, the port 106 may include an internally threaded, rigid, cylindrical wall 110 that releasably receives the threaded nozzle 113 of the cartridge 12. In the illustrated example, the cylindrical wall 110 has a central axis C that extends transversely from a longitudinal axis L of the stem portion 14.

Referring to FIGS. 2-3, a detachable, externally threaded plug 112 may be provided for closing the port 106 once the cartridge 12 is removed so that the mold 10 can be set down in any orientation while the material is curing in the interior cavity. The plug 112 may include at least one end surface 114 configured for both substantially blocking the port 106 and for forming a surface of a prosthesis or spacer body formed in the interior cavity 22. The plug 112 also may be generally cylindrical and have a cross brace or plate 116 to strengthen the plug.

Optionally, the stem portion 14 may have a second (or more) port 106a with its own plug 112a (shown in dashed line) spaced from port 106 along the stem portion 14 to provide the cement more directly to other parts of the cavity 22. This may better ensure the cement fills all parts of cavity 22. Also, since the cement has such a high viscosity, it is difficult for practitioners to comprehend that the cement gun creates sufficient pressure to place the cement throughout the spacer mold 10. Thus, a practitioner can use the open additional port 106a to determine by sight, if the cavity 22 is full, and then, if needed, provide extra cement to further fill other areas of cavity 22 around the additional port 106a such as by the lower end portion 56 of the stem portion 14 in the illustrated example.

The reinforcing bar 26 may be used to strengthen the spacer 200 and reduce the amount of cement material necessary to fill the spacer mold 10. To embed the reinforcing bar 76 in the spacer 200, the reinforcing bar 26 may be generally spaced from an interior surface 122 defining the cavity 22 so that cement can generally spread to all areas between the stem portion 14 and reinforcing bar 26. For this purpose, centering projections 124 extend outwardly from an outer surface 120 of the reinforcing bar 26 to engage the interior surface 122. Alternatively, the centering projections 124 are separate from the reinforcing bar 26 and extend from the stem portion 14 to hold the reinforcing bar 26 in the spaced position. At least one centering projection 126 extends from the reinforcing bar 26 and engages at least one corresponding, interiorly extending protrusion 128 extending from the interior surface 122 (or vice-versa) so that the reinforcing bar 26 is both centered away from interior surface 122 and is secured longitudinally, laterally, and/or rotationally relative to the stem portion 14. In one configuration, the protrusion 128 is generally ring shaped and receives the centering projection 126 in the protrusion's center. Here, two protrusion-projection engagements exist on opposite sides of the reinforcing bar 26. The reinforcing bar 26 is made of cast Co—Cr and has a generally widened disc-shaped, head portion 130 for extending into, and filling a portion of, the head molding chamber 46 as shown in FIG. 4.

Figure 8:
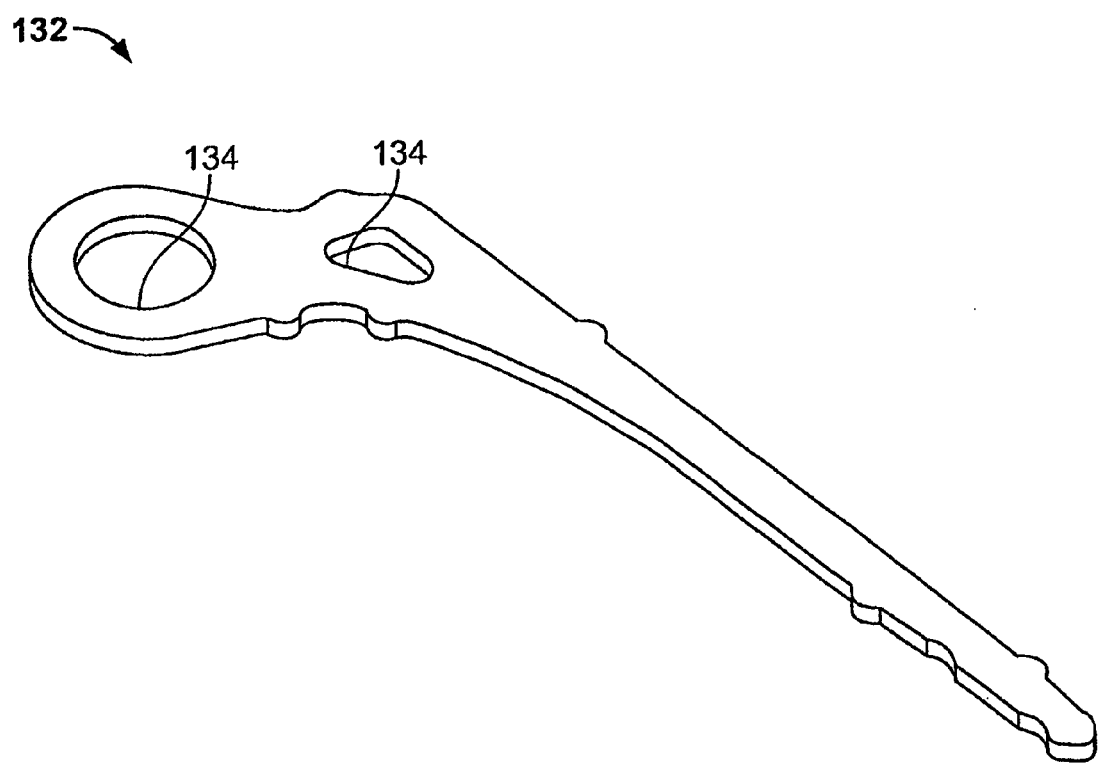
FIG. 8 is a side perspective view of an alternative reinforcing part in accordance with the present invention.

Alternatively, as shown in FIG. 8, an optional reinforcing bar 132 may be made of a generally flat piece of laser cut stainless steel. In this form, holes 134 are cut in the reinforcing bar 132 so that cement can extend through the holes 134. Once cured, the cement is interlocked with the reinforcing bar 132. These holes 134 can also be provided on reinforcing bar 26.

Referring again to FIGS. 1-2, the spacer mold stem members 18 and 20 are not permanently sealed so that pressure on the members 18 and 20 can open a thin space 152 between them to form vents 140 that permit gas or air to exhaust from the spacer mold 10 as the spacer mold is being filled with cement. The vents 140 also may provide a visual indication that the spacer mold is filled with cement when cement flows out of the vents 140. To provide the vents 140, the stem member 18 has front and back longitudinally extending flanges 142 and 144 that respectively oppose and align with front and back flanges 146 and 148 on the right stem member 20. So configured, the front flanges 142 and 146 and the back flanges 144 and 148 are held together by fasteners 150 (only one is shown in FIG. 2) that can clamp the left and right stem members 18 and 20 together. Space 152 (also shown on FIG. 5) exists between the corresponding front or back flanges to form the vents 140 between at least two fasteners 150 but may be between all fasteners or generally throughout the entire surface area of flanges 142, 144, 146, and 148. This space 152 may exist due to manufacturing tolerances. It will be appreciated, however, that the vents 140 could be alternatively or additionally formed by grooves or other openings on the flanges 142, 144, 146 and/or 148 or by openings anywhere else on the stem portion 14 or by intentionally tightening the fasteners 150 to a predetermined less-than-maximum amount of tension.

In the illustrated embodiment, the spacer mold 10 is provided to the physicians with the flanges 142 and 144, 146 and 148, pre-assembled to each other with the proper amount of tension to provide the vents 140 (and with the reinforcing bar 26 and stem-end mold piece 28 placed therein). Also in the illustrated form, flanges 142 and 144 on the left stem member 18 have an array of spaced fastener receiving collars 154 that extend transversely to the longitudinal axis L and align with collars 156 on the opposite corresponding flanges (144 and 148). The collars 154 and 156 receive and hold the fasteners 150. In the illustrated form, the spacer mold 10 has 15 fasteners 150 spread along the length of the spacer mold, although more or less could be used.

Figure 5:
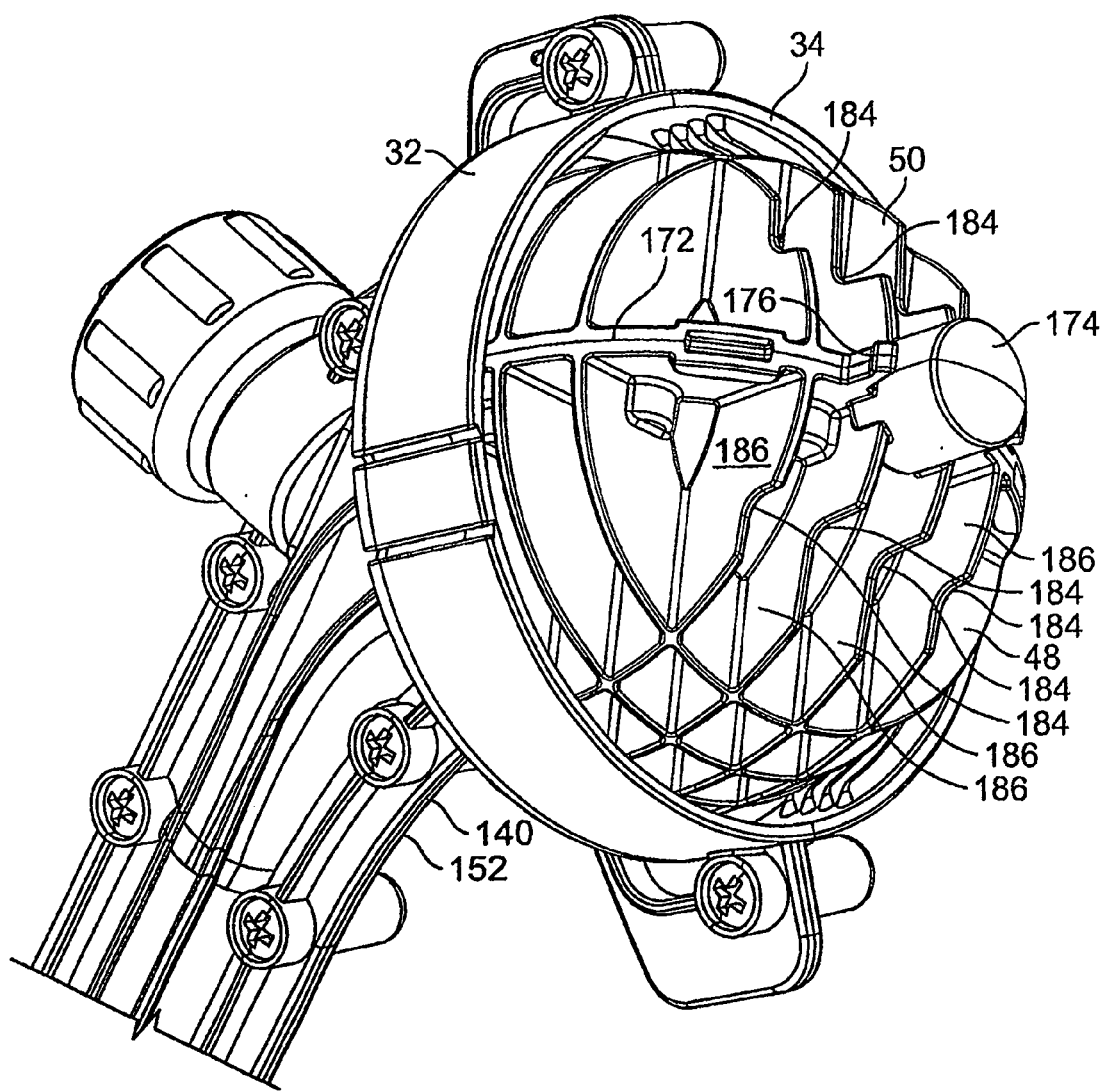
FIG. 5 is a fragmentary perspective view of an end of a stem portion of the spacer mold of FIG. 1 with a cover removed.

Referring to FIGS. 2-3 and 5, on the head portion 16, the securing member 54 has a cover portion 158 and an externally threaded cylindrical portion 160 that releasably engages the threaded cylindrical wall 42 on the upper portion 30 of the stem portion 14. So configured, the securing member 54 can be unscrewed from the upper portion 30 to release the head modules 48 and 50 from a cured spacer 200 formed therein. An annular strengthening flange 159 extends outward from a joint 161 of the cover portion 158 and cylindrical portion 160. The cover portion 158 and cylindrical portion 160 cooperatively define an interior 162 that receives the one or more head modules 48 and 50. The securing member 54 has a generally central opening or vent 164 on the cover portion 158.

Figure 11:
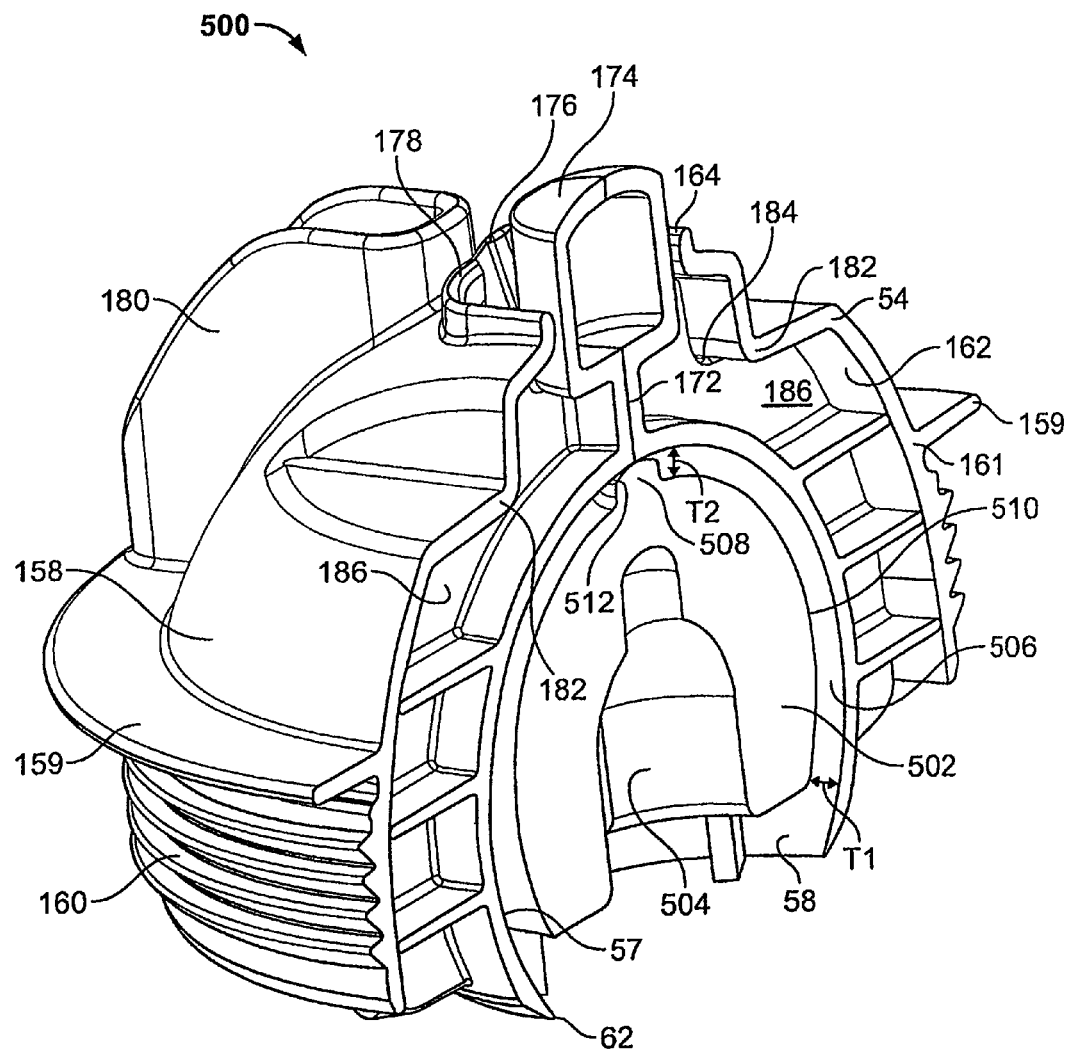
FIG. 11 is a perspective, cross-sectional view of another alternative head section of a spacer mold in accordance with the present invention.

The head modules 48 and 50 have opposing surfaces 166 (only one is shown in FIGS. 2-3) with pegs 168 on one head module 48 that fit in holes 170 on the other head module 50 and vice-versa. The securing member 54 holds the opposing surfaces 166 against each other and maintains the pegs 168 in the holes 170. As shown in FIG. 11, the inner diameter of the securing member 54, however, is slightly larger than the widest external dimension of the head modules 48 and 50 so that a slight opening or space 172 exists (shown in FIGS. 5 and 11) between the two head modules 48 and 50. In one form, the space 172 is about $8/1000$ inches wide. The space 172 may communicate with the vent 164 to permit gas from the head molding chamber 46 and interiorly of the head modules 48 and 50 to escape the spacer mold 10. In the illustrated form, the head modules 48 and 50 extend through the vent 164, and in turn, define the space 172 to extend through vent 164 so that gas from between the head modules 48 and 50 may be released. The head modules 48 and 50 may also have snap-fit barbs 176 to engage an upper wall 178 of the cover portion 158 to secure the head modules 48 and 50 to the securing member 54. An extension 174 on the head modules 48 and 50 extends upward into the vent 164. The extension 174 is used as leverage by pressing the extension 174 to hold the head portions 48 and 50 in place while gripping and rotating the securing member 54 to detach the securing member 54 from the stem portion 14 and the head portions 48 and 50. This will overcome the snap-fit and any adhesion between the cover portion 158 and head portions 48 and 50 caused by cement. The securing member 54 may also have handles 180 extending upwardly on the cover portion 158 to facilitate the rotation.

Still referring to FIG. 11, the cover portion 158 also has two opposing protrusions 182 that project interiorly into the interior 162 of the securing member 54. The protrusions 182 engage grooves 184 (shown best on FIG. 5) on an array of bracing flanges 186 that form the exterior of the head modules 48 and 50. With the protrusions 182 seated within the grooves 184 on the bracing flanges 186, the head modules 48 and 50 will rotate with the securing member 54 when the securing member 54 is being removed from the stem portion after curing the spacer 200. This facilitates breaking bonds between the dried cement of the head portion 202 of the spacer 200 and the interior arcuate surfaces 57 and 58 of the head modules 48 and 50. Once the securing member 54 is removed, the head modules 48 and 50 can be peeled or otherwise pulled off of the head portion 202.

Figure 9:
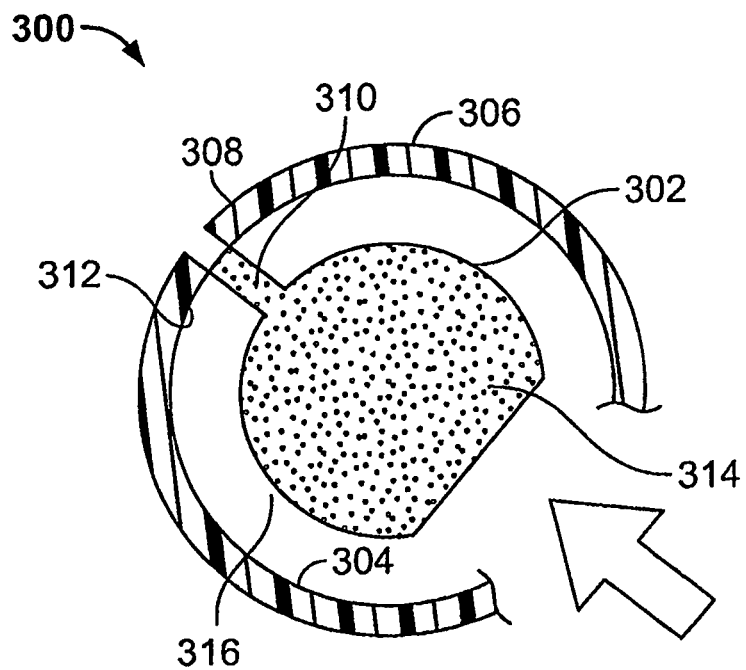
FIG. 9 is a simplified, side cross-sectional view showing an alternative head section for a spacer mold in accordance with the present invention.

Referring to FIG. 9, in one alternative head portion 300, a porous core 302 made of polyethylene is provided within the interior space 304 formed by at least one head module or cover 306. A cavity 312 is defined between the core 302 and the head module 306 to receive cement. The head module 306 defines a centrally located vent passage 308 to release gas from within the interior space 304. A porous extension 310 on the core 302 abuts the cover 306 adjacent the vent passage 308 and a network of pores 314 on the core 302 provides air passage from the cavity 312 to the vent passage 308. With this configuration, cement fills cavity 312, and then fills pores 314 and the extension 310 of the core 304. This directs air from the interior spacer 304 within the cover 306 into the pores 314, and out of extension 310 and, in turn, through the vent passage 308. An outer surface 316 of the core 302 provides a relatively large surface area to receive and remove gas from within the interior space 304. The core 302 may replace a reinforcing bar head or the reinforcing bar head may be embedded within the core 302.

Figure 10:
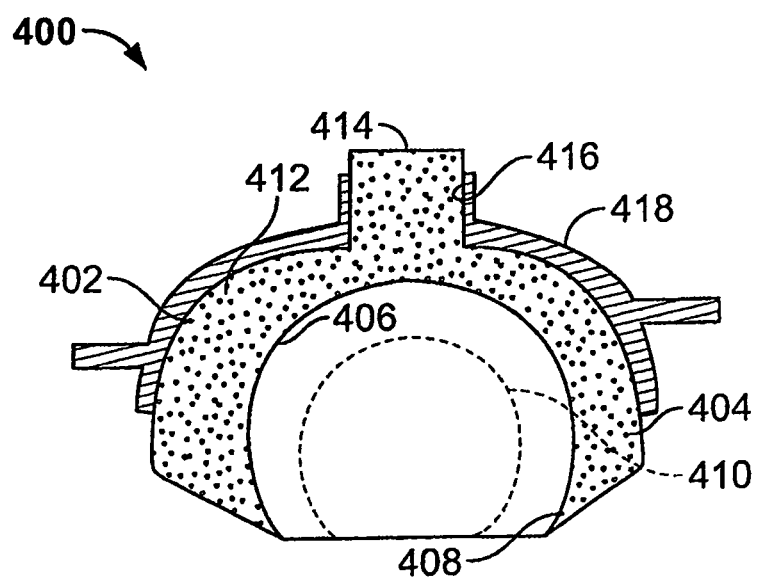
FIG. 10 is a simplified, side cross-sectional view showing another alternative head section for a spacer mold in accordance with the present invention.

Referring to FIG. 10, in another alternative head portion 400, head modules 402 and 404 have generally the same basic shape as head modules 48 and 50 but are made of a porous material as with core 302. The head modules 402 and 404 will provide a relatively large surface area for receiving and disposing of gas from within an interior space 406. A reinforcing head 410 may or may not be disposed within cavity 408 as desired. Cement filling the interior space 408 will force gas from the interior space 408, and into pores or a network of pores 412 on the interior surface 406. The pores 412 provide passages to an extension 414 on the head modules 402 and 404. The extensions 414 extend out of a vent passage 416 defined by a cover 418 to exhaust the gas. The cover 418 secures the head modules 402 and 404 to stem portion 14.

Referring again to FIG. 11, in yet another alternative head portion arrangement 500, a solid core 502 of steel, Co—Cr, or hard polymers may be provided rather than a porous core. In this case, however, the solid core 502 has an inner space 504 to receive reinforcing bar head 130 of reinforcing bar 26. The core 502 and at least one head module 504 cooperatively define a molding cavity 506 therebetween that has a varying thickness in order to control the flow of the cement. More specifically, the molding cavity 506 progresses from a maximum thickness T1 proximal to the stem portion 14 to a minimal thickness T2 distal to the stem portion 14 and adjacent the vent 172 on or between the head module 48 and 50. This is accomplished by opposing a tapered outer surface 510 of the core 502 with the spherical surfaces 57 and 58 of the head modules 48 and 50. It will be understood that surfaces 57 and 58 could by alternatively or additionally tapered instead. Otherwise, the head portion 500 has securing member 54 and head modules 48 and 50 as with head portion 16. The core 502 may also have an upper spacing projection 508 that extends outward from outer surface 510 and engages surfaces 57 and 58 to maintain the interior space 506. The projection 508 has a curved, spherical-like surface 512 to engage the surfaces 57 and 58 so as not to substantially block vent 172.

It will also be understood that venting of gases may take place at other locations as well, such as between the plug and port 106 (while the cement is setting), between the lower wall 104 of the stem portion 14 and the stem-end mold piece flanges 102 or 103, between the pin 76 and the slot 84, and between the cylindrical wall 42 of the stem portion 14 and the wall 160 of the securing member 54, for example.

Referring again to FIG. 3, as another optional feature of the spacer mold 10, a compliance element 188 (shown in dashed line) may be disposed within the cavity 22 and between the reinforcing bar 126 and the interior surface 122 of the stem portion 14 so that the compliance element 188 is at least partially embedded within the spacer 200. The compliance element 188 compresses when the curing material is placed in the interior cavity 22 and on the compliance element 188. This results in the compliance element 188 applying a force to urge the cement against the interior surface 122 of the stem portion 14. This also restricts or reduces the amount of trapped gas within the cement. The compliance element 188 may be a balloon or other enclosed mechanical device with a spring, or other device that applies an outwardly directed force from within the spacer 200.

While in one form, the spacer mold 10 is completely assembled before the gun cartridge 12 is used to inject cement into the spacer mold 10. In an alternative form, cement is placed within sections of the spacer mold 10 before the spacer mold 10 is fully assembled. In this example, securing member 54 is placed upside-down and the head modules 48 and 50 are placed in the securing member 54. The head modules 48 and 50 are then filled with cement before attaching the head modules 48 and 50 and securing member 54 to the stem portion 14.

Similarly, the stem portion 14 may be at least partially filled with cement before the head portion 16 is attached to the stem portion 14. The stem portion 14 may be filled either through the port 106 or through an opening 198 (shown in FIG. 4) on the upper end portion 30 of the stem portion 14. The opening 198 provides passage from the head molding chamber 46 to the cavity 22 in the stem portion 14.

In one case, after both the head and stem portions 14 and 16 are separately filled with cement, the head portion 16 is connected to the stem portion 14 for integrally forming the spacer head 202 with spacer stem 204. Optionally, a cement gun may be connected to the port 106 to further fill the spacer mold 10 with cement after the stem portion 14 and the head portion 16 are connected together. This may collapse air pockets existing in the cement. In such a case, the cement may or may not be injected under relatively high pressure.

Referring again to FIGS. 1-2, in order to remove the cured spacer 200 from the spacer mold 10, the securing member 54 is unscrewed from the stem portion 14 and the head modules can be pulled away from the spacer 200. The spacer mold 10 also has at least one generally longitudinally extending, removable section 190 on one or both of the stem members 18 and 20. In the illustrated form, the removable section 190 is disposed between two thinned strips 192 where the removable section 190 and the thinned strips 192 are integrally formed with a body or remainder 194 of the material forming the stem members 18 and 20. Thus, the thinned strips 192 connect the removable section 190 to the body 194 of the spacer mold 10. The thinned strips 192 have a sufficient thickness to withstand the lateral impact forces of the pressurized cement from within the spacer mold 10 but are sufficiently thin to tear when pulled longitudinally. One or more of the removable sections 190 may have at least one grasping portion, such as a generally annular ring 196, connected to the at least one removable section 190 so that the grasping portion 196 can be held and pulled to remove the removable section 190 from the body 194. Grasping portion 196 can be pulled by hand but also may be removed by tool such as by a roll-up bar placed through a ring and then rolled to roll up the removable sections 190 on the bar. In one example, the grasping portion 196 is integrally formed with the removable section 190. Once the removable section 190 is removed from the body 194 and the spacer 200, the rest of the spacer mold body 194 can be removed from the spacer 200 with tools to press, pull, or peel the mold body 194 away from the spacer 200 or to break the body 194 into smaller removable pieces.

While this invention has been described as having preferred embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A mold comprising:
a body having a head end and a stem end and defining an interior cavity having a length, the head end including at least one removable section and at least one grasping portion connected to the at least one removable section;
a port in communication with the interior cavity and configured to be in releasable connection to a pressurized injector;
an adjusting member slidingly engaged with the body at the stem end, the adjusting member including a plurality of selectable positions to vary the length of the interior cavity; and
a retaining mechanism configured to releasably engage the adjusting member at any one of the plurality of selectable positions, wherein the retaining mechanism is outwardly biased to retain the adjusting member in a select position.

2. The mold of claim 1, the adjusting member further including a cupped portion configured to form a rounded stem end of a molded object.

3. The mold of claim 1, wherein the plurality of selectable positions corresponds to a respective plurality of positions of the cupped portion within the interior cavity length.

4. The mold of claim 3, wherein each one of the plurality of selectable positions comprises a hole or a slot.

5. The mold of claim 3, wherein the retaining mechanism includes a flexible member.

6. The mold of claim 5, wherein the stem end further comprises a passage extending transverse to the interior cavity length and having a passage opening and a closed end opposite the passage opening, the closed end configured to engage an end of the flexible member.

7. The mold of claim 6, wherein the retaining mechanism is inserted into the passage opening to releasably engage a select one of the plurality of selectable positions.

8. The mold of claim 1, wherein the retaining mechanism comprises a pin.

9. The mold of claim 6, wherein the retaining mechanism is outwardly biased at the flexible member end.

10. The mold of claim 9, wherein the passage closed end comprises at least one tapered section and wherein the outwardly biased flexible member end engages the at least one tapered section.

11. The mold of claim 1, wherein the body further comprises at least one grasping portion adjacent the head end.

12. The mold of claim 11, wherein the grasping portion is generally annular.

13. The mold of claim 11, wherein the body further comprises at least one removable section adjacent the head end.

14. The mold of claim 13, wherein the at least one grasping portion is integrally formed with the at least one removable section.

15. The mold of claim 13, wherein the at least one grasping portion comprises at least two grasping portions and the at least one removable section comprises at least two removable sections.

16. The mold of claim 1, further comprising a plug configured for placement in at least a portion of the port.

17. The mold of claim 5, wherein the retaining mechanism is configured to engage a select one of the plurality of selectable positions when the select one of the plurality of selectable positions is disposed adjacent the passage.

18. An adjustable mold, comprising:
an adjusting member comprising a cupped portion configured to form a rounded end of a molded object and a positioning member defining a plurality of selectable positions;
a body member having a longitudinal axis and an end portion, the end portion including an opening configured to receive the adjusting member and a passage extending transverse to the longitudinal axis, the passage having a passage opening and a closed end opposite the passage opening; and
a retaining mechanism configured to be received in the passage opening and outwardly biased to releasably engage the passage closed end,
wherein the body member and the adjusting member cooperate to define a mold cavity having a length, and the adjusting member is movably engaged with the body member to vary the mold cavity length when the mold is fully assembled.

19. The mold of claim 18, wherein the plurality of selectable positions of the positioning member correspond to a respective plurality of axial positions of the cupped portion within the mold cavity.

20. The mold of claim 18, wherein the retaining mechanism is further configured to releasably engage the positioning member.

21. The mold of claim 20, wherein the retaining mechanism is configured to releasably engage any one of the plurality of selectable positions.

22. The mold of claim 21, wherein the retaining mechanism is configured to engage a select one of the plurality of selectable positions when the select one of the plurality of selectable positions is disposed adjacent the passage.

23. The mold of claim 22, wherein the retaining mechanism is inserted into the passage opening to releasably engage the select one of the plurality of selectable positions.

24. The mold of claim 20, wherein the retaining mechanism is configured to releasably engage a hole or a slot in the positioning member.

25. The mold of claim 18, wherein the retaining mechanism comprises a pin.

* * * * *